United States Patent [19]
Kjell et al.

[11] Patent Number: 6,013,828
[45] Date of Patent: Jan. 11, 2000

[54] PROCESSES AND INTERMEDIATES USEFUL TO MAKE ANTIFOLATES

[75] Inventors: Douglas Patton Kjell, West Lafayette; Brian James Slattery, Lafayette; Charles Jackson Barnett, Indianapolis, all of Ind.

[73] Assignee: Eli Lilly and Company, Indianapolis, Ind.

[21] Appl. No.: 09/160,129

[22] Filed: Sep. 24, 1998

Related U.S. Application Data

[60] Provisional application No. 60/093,039, Sep. 26, 1997.

[51] Int. Cl.$^7$ .......................... C07C 315/00; C07C 69/76
[52] U.S. Cl. ................................. 560/11; 560/8; 560/19; 560/38
[58] Field of Search ................................. 560/8, 11, 12, 560/18, 19, 38

[56] References Cited

U.S. PATENT DOCUMENTS

| | | | |
|---|---|---|---|
| 5,349,064 | 9/1994 | Akimoto et al. | 544/280 |
| 5,416,211 | 5/1995 | Barnett et al. | 544/280 |
| 5,496,946 | 3/1996 | Akimoto et al. | 544/321 |

FOREIGN PATENT DOCUMENTS

| | | |
|---|---|---|
| 314280 A2 | 9/1988 | European Pat. Off. . |
| 438261 A2 | 1/1991 | European Pat. Off. . |
| 589720 A2 | 9/1993 | European Pat. Off. . |

OTHER PUBLICATIONS

Taylor et al., A Convergent Synthesis of 5,10–Dideaza–5,6,7,8–tetrahydrofolic Acid and 5,10–Dideaza–5,6,7,8–tetrahydrohomofolic Acid. An Effective Principle for Carbonyl Group Activation, *J. Org. Chem.*, 55(10), 3222–3227 (1990).

Larock et al., Synthesis of Aryl–Substituted Aldehydes and Ketones Via Palladium–Catalyzed Coupling of Aryl Halides and Non–Allylic Unsaturated Alcohols, *Tetrahedron Letters*, 30(48), 6629–6632 (1989).

Khusid et al., Regeneration of Aldehydes from Their Bisulfite Derivatives in Water and organic Solvents on Ion–Exchange Resins, *Zhurnal Organicheskoi Khimii.*, 21(1), pp. 43–45 (1985).

Vinczer et al., An Improved Synthesis of 5–Hydroxypentanal, *Org. Prep. Proced. Int.*, 21(3), 344–346 (1989).

Schlecht et al., Bicycloannulation of 3–Indolylenamines with Cyclohexenone: A Facile Preparation of Potential Neurotransmitter Analogs, Heterocycles, 25(1), 485–491 (1987).

Takahashi et al., Efficient Synthesis of 1–Substituted, 2,5–Dicyanopyrrolidines by The Strecker Reaction Using Succinaldehyde and Primary Amines, and Their Stereochemistry, *Heterocycles*, 24(10), 2905–2910 (1986).

Wuts et al., The Oxidation of Aldehyde Bisulfite Adducts to Carboxylic Acids and Their Derivatives with Dimethylsulfoxide and Acetic Anhydride, *Tetrahedron Letters*, 27(34), 3995–3998 (1986).

Taub et al., Interconversion of Adrenal Cortical Side Chains. The Transformation of Cortisone and Hydrocortisone to Corticosterone, *J. Am. Chem. Soc.*, 76, 4094–4097 (1954).

Taylor et al., A Ring–Transformation/Ring–Annulation Strategy for the Synthesis of the DHFR Inhibitor, TNP–351: A Correction *J. Org. Chem.*, 61(22), 7973–7974 (1996).

Taylor et al., A Fischer–Indole Approach to Pyrrolo[2,3–d] Pyrimidines, *Heterocycles*, 43(2), 323–338 (1996).

Taylor et al., Diels–Alder Reactions of 6–Azapterins, An Alternative Strategy for the Synthesis of 5,10–Dideaza–5, 6,7,8–Tetrahydrofolic Acid (DDATHF), *Heterocycles*, 27(8), 1925–1928 (1988).

DeGraw et al., Synthesis of 5,10–Dideazaminopterin, *J. Heterocyclic Chem.*, 23(1), 1–4 (1986).

Taylor et al., Synthesis of a Regioisomer of N–{4–[2–(2–Amino–4 (3H)–Oxo–7H–Pyrrolo[2,3–d] Pyrimidine–5–yl) Ethyl]Benzoyl}–L–Glutamic Acid (LY231514), An Active Thymidylate Synthase Inhibitor and Antitumor Agnet, *Heterocycles*, 36(8), 1897–1908 (1993).

*Primary Examiner*—Alan L. Rotman
*Assistant Examiner*—Charanjit S. Aulakm
*Attorney, Agent, or Firm*—Gilbert T. Voy; John C. Demeter

[57] ABSTRACT

The present application relates to a series of novel sulfonic acid metal cation salts of the formula

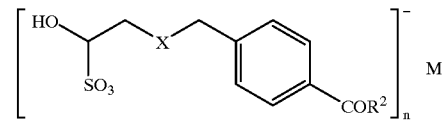

which are useful intermediates to prepare antifolate 5-substituted pyrrolo[2,3-d]pyrimidines. The present invention also relates to a novel process for preparing the sulfonic acid metal cation salts and to a novel process for preparing aldehydes of the formula

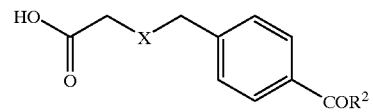

from the corresponding sulfonic acid metal cation salts.

15 Claims, No Drawings

PROCESSES AND INTERMEDIATES USEFUL TO MAKE ANTIFOLATES

CROSS-REFERENCE

This application claims the benefit of U.S. application No. 60/093,039 with an accorded filing date of Sep. 26, 1997 which, pursuant to 37 C.F.R. 1.53(b)(2)(ii), is a conversion of U.S. application Ser. No. 08/938,385, filed Sep. 26, 1997.

FIELD OF THE INVENTION

This invention relates to synthetic organic chemistry. Specifically, the invention relates to a process for preparing intermediates useful in the syntheses of valuable antifolate compounds.

BACKGROUND OF THE INVENTION

Compounds known to have antifolate activity are well recognized as chemotherapeutic agents for the treatment of cancer. Recently, a series of 5-substituted pyrrolo[2,3-]pyrimidine compounds of formula XVI:

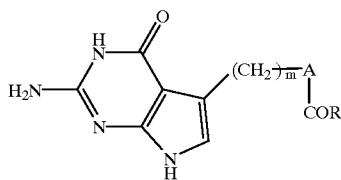

XVI where R is NHC*H(CO$_2$R$^1$)CH$_2$CH$_2$CO$_2$R$^1$ or OR$^1$, the configuration about the carbon atom designated * is L, each R$^1$ is hydrogen or the same or different carboxy protecting group, m is 2 or 3, and A is an aryl group; and their pharmaceutically acceptable salts were disclosed as antifolates or intermediates to antifolates. U.S. Pat. No. 5,416,211 (U.S. '211).

A key intermediate to compounds of formula XVI is the α-halo aldehyde of formula XV:

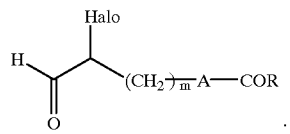

XV

Among the possible routes to compounds of formula XV disclosed in U.S. '211, alpha halogenation of aldehydes of formula XIV:

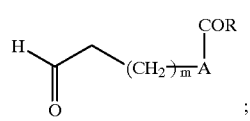

XIV is most direct.

A synthesis published by Taylor and Harrington teaches the route to compounds of formula XIV shown below:

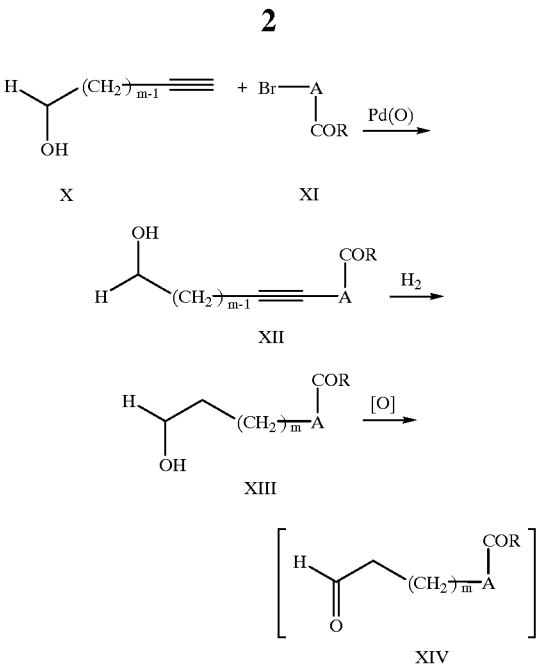

Taylor, E. C., Harrington, P. M., *J.Org.Chem.*, 55, 3222, (1990).

Another synthesis published by Larock, et. al., may be used to form the requisite aldehydes of formula XIV by a similar palladium[0] catalyzed coupling shown below:

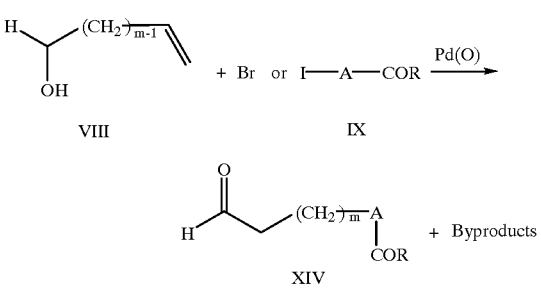

Larock, R. C., Leung, W., Stolz-Dunn, S., *Tet.Let.*, 30, 6629, (1989).

If the procedure of Larock is followed, a mixture of desired and undesired products results, the components of which are very difficult to separate and purify to afford compounds of formula XIV. In addition, regardless of how they are formed, aldehydes of formula XIV are typically not isolated, due to their inherent instability, and are instead alpha halogenated in situ to provide the alpha halo aldehydes of formula XIX, as disclosed in U.S. '211.

An improvement over the prior art would provide a facile method for selectively producing a compound of formula XIV and would provide an aldehyde analogue amenable to isolation, bulk manufacturing, and storage easily convertible to it's aldehyde form.

SUMMARY OF THE INVENTION

The present invention relates to compounds of formula IV:

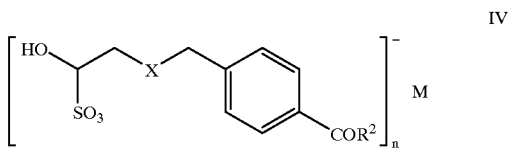

where:
M is a metal cation;
n is 1 or 2;
$R^2$ is $NHCH(CO_2R^3)CH_2CH_2CO_2R^3$ or $OR^3$;
$R^3$ is independently at each occurrence a carboxy protecting group; and
X is a bond or $C_1$–$C_4$ alk-diyl, which are useful intermediates to those antifolate 5-substituted pyrrolo[2,3-d] pyrimidines disclosed in U.S. '211 that correspond to the substitution parameters of the compounds of formula IV.

The present invention further relates to a process for preparing compounds of formula III:

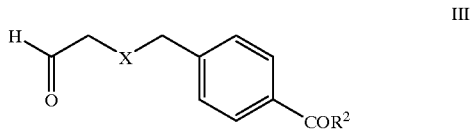

where:
$R^2$ is $NHCH(CO_2R^3)CH_2CH_2CO_2R^3$ or $OR^3$; and
$R^3$ is independently at each occurrence a carboxy protecting group;
which comprises reacting a compound of formula IV with a trialkylsilyl halide in a solvent.

The invention also relates to a process for preparing a compound of formula IV which comprises reacting a compound of formula III with a compound of the formula $M(HSO_3^-)_n$ in a solvent.

DETAILED DESCRIPTION OF THE INVENTION

The compounds of formula IV where $R^2$ is $OR^3$ are enantiomeric and the compounds of formula IV where $R^2$ is $NHCH(CO_2R^3)CH_2CH_2CO_2R^3$ are diastereomeric. Single enantiomers, single diastereomers, and mixtures thereof are encompassed within the scope of this invention. It is preferred that the chiral center in the glutamic acid residue ($R^2$ is $NHC^*H(CO_2R^3)CH_2CH_2CO_2R^3$ where $C^*$ is the chiral center), when present, be of the "L" configuration.

In the present document, all expressions of concentration, percent, ratio and the like will be expressed in weight units unless otherwise stated, except for mixtures of solvents which will be expressed in volume units. All temperatures not otherwise stated will be expressed in degrees Celsius. Compounds or compound mixtures in brackets, except those brackets used to denote salt forms, signify intermediates which are preferably not isolated before their use in subsequent reactions.

In the general formulae of the present document, the general chemical terms have their usual meanings. For example, the term "alkyl" refers to a fully saturated, straight or branched chain, monovalent hydrocarbonyl moiety having the stated number of carbon atoms and includes, but is not limited to, a methyl, ethyl, propyl, isopropyl, n-butyl, s-butyl, and t-butyl groups, and also includes higher homologs and isomers thereof where appropriate.

The term "$C_1$–$C_4$ alk-diyl" refers to a fully saturated straight chain divalent hydrocarbon moiety having from 1 to 4 carbon atoms wherein each carbon atom in the chain may be independently substituted once with a $C_1$–$C_4$ alkyl group. For example, 1,2-dimethylprop-1,3-diyl is encompassed within the definition of $C_1$–$C_4$ alk-diyl but 1,1-dimethylprop-1,3-diyl is not. The term is further exemplified by moieties such as, but not limited to, —$CH_2$—, —$CH_2CH_2$—, —$CH_2(CH_2)CH_2$—, methyleth-1,2-diyl, —$CH_2(CH_2)_2CH_2$—, and but-1,3-diyl. Preferred $C_1$–$C_4$ alk-diyl groups are those that are unsubstituted and most preferred are —$CH_2$— and —$CH_2CH_2$—.

The term "$C_2$–$C_6$ alkenyl" refers to a mono-unsaturated, monovalent, hydrocarbon moiety containing from 2 to 6 carbon atoms which may be in a branched or straight chain configuration. The term is exemplified by moieties such as, but not limited to, ethylenyl, propylenyl, allyl, butylenyl, and pentylenyl.

The term "$C_1$–$C_4$ alkoxy" refers to a methoxy, ethoxy, propoxy, isopropoxy, butoxy, s-butoxy, and a t-butoxy group.

The term "halo" and "halide" refers to chloride, bromide, or iodide.

The terms "substituted benzyl", "substituted benzhydryl", and "substituted trityl" refers to a benzyl, benzhydryl, and trityl group, respectively, substituted from 1 to 5 times independently with a nitro, $C_1$–$C_4$ alkoxy, $C_1$–$C_6$ alkyl, or a hydroxy($C_1$–$C_6$ alkyl) group. These substitutions will only occur in a sterically feasible manner such that the moiety is chemically stable.

The terms "substituted $C_1$–$C_6$ alkyl" and "substituted $C_2$–$C_6$ alkenyl" refer to a $C_1$–$C_6$ alkyl and $C_2$–$C_6$ alkenyl group respectively substituted from 1 to 3 times independently with a halo, phenyl, tri($C_1$–$C_4$ alkyl)silyl, or a substituted phenylsulfonyl group.

The terms "substituted phenyl" and "substituted phenylsulfonyl" refer to a phenyl and phenylsulfonyl group respectively where the phenyl moiety of either is para substituted with a $C_1$–$C_6$ alkyl, nitro, or a halo group.

The term "leaving group" refers to a monovalent substituent of a molecule which is prone to nucleophilic displacement. Typical leaving groups include, but are not limited to, sulfonates such as phenyl, substituted phenyl, $C_1$–$C_6$ alkyl, and $C_1$–$C_6$ perfluoro alkylsulfonates; halides; and diazonium salts such as diazonium halides.

The term "carboxy protecting group" as used in this specification denotes groups which generally are not found in the final therapeutic compounds but are intentionally introduced during a portion of the synthetic process to protect a group which otherwise might react in the course of chemical manipulations, and is later removed. Examples of such carboxylic acid protecting groups include $C_1$–$C_6$ alkyl, substituted $C_1$–$C_6$ alkyl, $C_2$–$C_6$ alkenyl, substituted $C_2$–$C_6$ alkenyl, benzyl, substituted benzyl, benzhydryl, substituted benzhydryl, trityl, substituted trityl, trialkylsilyl, aroyl groups such as phenacyl, and like moieties. The species of carboxy-protecting group employed is not critical so long as the derivitized carboxylic acid is stable to the conditions of subsequent reaction(s) on other positions of the molecule and can be removed at the appropriate point without disrupting the remainder of the molecule. Carboxy protecting groups similar to those used in the cephalosporin, penicillin, and peptide arts can also be used to protect a carboxy group substituent of the compounds provided herein. Futher examples of these groups are found in E. Haslam, "Protective Groups in Organic Chemistry", J. G. W. McOmie, Ed., Plenum Press, New York, N.Y., 1981, Chapter 5 and T. W. Greene, "Protective Groups in Organic Synthesis", 2nd Ed., John Wiley and Sons, New York, N.Y., 1991, Chapter 5. When $R^1$ or $R^3$ is a carboxy protecting group, the protecting group is preferably $C_1$–$C_4$ alkyl. The most preferred protecting groups are methyl and ethyl.

The term "trialkylsilyl" refers to a monovalent silyl group substituted 3 times independently with a $C_1$–$C_6$ alkyl group.

The term "trialkylsilyl halide" refers to a compound of the formula $(C_1$–$C_6$ alkyl$)_3$—Si—halo wherein each $C_1$–$C_6$ alkyl is the same or different. Trialkylsilyl halides include, but are not limited to, trimethylsilyl, triethylsilyl, tripropylsilyl chloride, bromide, and iodide.

The term "metal cation" refers to an alkali or alkaline earth metal cation. Alkali metals form singly charged cations, e.g., $Li^{+1}$, $Na^{+1}$, and $K^{+1}$, while alkaline earth metals form doubly charged cations, e.g., $Mg^{+2}$ and $Ca^{+2}$ but the charge on the compounds of formula IV, on compounds of the formula $M(HSO_3^-)_n$, or on metal cation chlorides as a whole, is zero. Therefore, when M is a Group I metal, the molar ratio between cation and anion is 1:1 and when M is a Group II metal cation, the molar ratio is 1:2.

The term "pharmaceutical salt" as used herein, refers to salts prepared by reaction of the compounds of the present invention with a mineral or organic acid (e.g. hydrochloric, hydrobromic, hydroiodic, or p-toluenesulfonic acid) or an inorganic base (e.g. sodium, potassium, lithium, magnesium, or hydroxide, carbonate, or bicarbonate). Such salts are known as acid addition and base addition salts. For further exemplification and methods of preparing pharmaceutical salts, see e.g. Berge, S. M, Bighley, L. D., and Monkhouse, D. C., *J. Pharm. Sci.*, 66, 1, 1977.

The term "phase transfer catalyst" refers to a salt in which the cation has large nonpolar substituent groups which confer good solubility on the salt in organic solvents. The most common examples are tetraalkylammonium and tetraalkylphosphonium ions e.g. tetraalkylammonium chloride or bromide.

The term "palladium catalyst" refers to a reagent which is a source of palladium zero (Pd(0)). Suitable sources of Pd(0) include, but are not limited to palladium(0) bis (dibenzylidineacetone) and palladium(II) acetate.

The term "halogenating reagent" refers to a reagent that can provide an electrophilic source of a halogen to the target molecule. Typical halogenating reagents include but are not limited to benzeneseleninyl chloride, bromide, or iodide, thionyl bromide or chloride, dibromobarbituric acid, N-bromo-, N-iodo-, and N-chloro succinimide, elemental chlorine, elemental bromine (and complexes of bromine such as bromine dioxane complex), and elemental iodine, and the like.

The term "thermodynamic base" refers to a base which provides a reversible deprotonation of an acidic substrate or is a proton trap for those protons that may be produced as byproducts of a given reaction, and is reactive enough to effect the desired reaction without significantly effecting any undesired reactions. Examples of thermodynamic bases include, but are not limited to, acetates, acetate dihydrates, carbonates, bicarbonates, and hydroxides (e.g. lithium, sodium, or potassium acetate, acetate dihydrate, carbonate, bicarbonate, or hydroxide), tri-($C_1$–$C_4$ alkyl)amines, or aromatic nitrogen containing heterocycles (e.g. imidazole and pyridine).

The term "suitable solvent" refers to any solvent, or mixture of solvents, inert to the ongoing reaction that sufficiently solubilizes the reactants to afford a medium within which to effect the desired reaction.

Compounds of formula IV may be prepared by a novel process illustrated in Scheme 1 below where Lg is a leaving group, $R^4$ is hydrogen or $C_1$–$C_4$ alkyl, and X' is $C_1$–$C_4$ alk-diyl;

with the proviso that if X' is not a bond, then the carbon alpha to the alcohol must be a —$CH_2$— moiety; and n, $R^2$ and X are as defined above for formula IV.

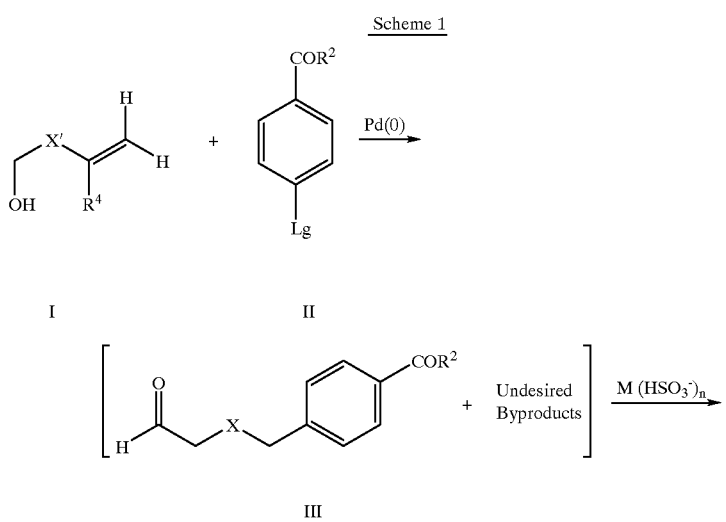

-continued

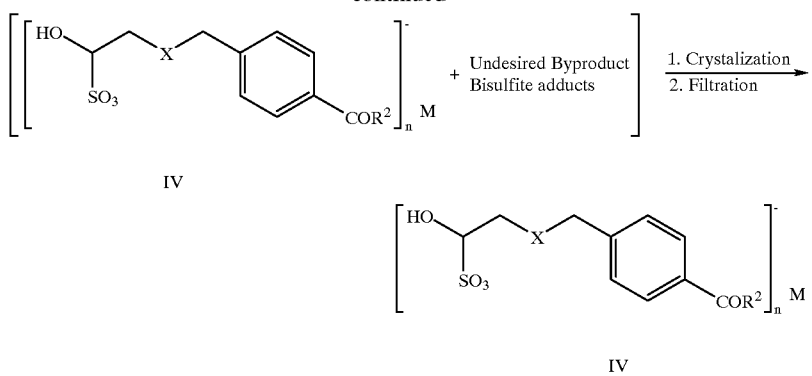

IV

A mixture containing a compound of formula III may be prepared by dissolving or suspending a compound of formula II in a suitable solvent, in the presence of a suitable thermodynamic base and a phase transfer catalyst, optionally in the presence of a metal cation chloride, and adding a compound of formula I and a palladium catalyst. Once all the reactants are combined, the reaction may be conducted at temperatures ranging from at least about 0° C. to about 100° C. Within this broad temperature range, when Lg is bromide in compounds of formula II, the reaction mixture should be heated to at least about 50° C., more preferably at least about 60° C., and most preferably at least about 65° C. for from about 8 to about 24 hours. When Lg is iodide, the reaction proceeds more robustly, thus a temperature range of 0° C. to about 25° C. is the typical temperature range with room temperature being the preferred reaction temperature. The reaction is preferably allowed to run for from 8 to about 10 hours.

Suitable solvents for this reaction include, but are not limited to, dimethylsulfoxide, tetrahydrofuran, N,N'-dimethylimidazole, diethyl ether, dimethoxyethane, dioxane, acetonitrile, mixtures thereof, and the like. Typically, an alkali metal acetate is generally the preferred thermodynamic base, and lithium acetate is the particularly preferred base. However, when Lg is bromo, lithium acetate dihydrate is the preferred base. In general, dimethylformamide or dimethylacetamide is the preferred solvent. Tetrabutylammonium bromide is generally the preferred phase transfer catalyst. Palladium(II) acetate is typically the preferred palladium catalyst. Although not required, it is preferred to employ an alkali metal chloride in order to maximize the yield of the desired product of formula III. Lithium chloride is the preferred metal cation chloride. Preferred compounds of formula I are those where $R^4$ is hydrogen and X' is a bond, —$CH_2$—, or —$CH_2CH_2$—,. In compounds of formula II, Lg is preferably bromo, iodo, or trifluoromethylsulfonyloxy. The most preferred Lg moiety is iodo. The most preferred compound of formula I is 3-butenol.

Relative to the compounds of formula II, the following amounts of preferred reagents are typically employed:
thermodynamic base—1.0 to about 3.0, preferably about 1.05 to about 1.3 equivalents;
metal cation chloride—0 to about 4, preferably about 2.8 to about 3.2 equivalents;
phase transfer catalyst—0 to about 3.0, preferably 0.4 to about 0.6 equivalents; and
palladium catalyst—0.015 to about 0.1, preferably about 0.02 to about 0.03 equivalents.
compound of formula I—1.0 to about 2.0, preferably about 1.1 to about 1.3 equivalents.

The reaction discussed above results in a mixture of products which includes a compound of formula III, which may be isolated but is preferably further reacted as described in Scheme 1. Substantial purification of the compound of formula III or separation from the undesired byproducts is not necessary before proceeding to the next novel step in the overall process. Preferably, a simple extraction using an aqueous immiscible solvent followed by filtration of the palladium catalyst is all that is performed before proceeding. Suitable solvents for the extraction include, but are not limited to, methylene chloride, chloroform, methyl acetate, carbon tetrachloride, mixtures thereof, and the like. The preferred solvent is typically ethyl acetate.

A metal bisulfite reactant of the formula $M(HSO_3^-)_n$ may be added to the organic extract filtrate from above (the mixture that contains a compound of formula III and byproducts). Typically, a lower alcohol, preferably ethanol 5% denatured with methanol (3A ethanol) or ethanol 0.5% denatured with toluene (2B-3 alcohol), and water are also added as co-solvents for this reaction. The volume of ethanol added is preferably about equal to that of the ethyl acetate originally present while the volume of water in the mixture is proportional to the volume of denatured ethanol, preferably at a ratio of about 1:5. Suitable metal bisulfite reactants include, but are not limited to, sodium bisulfite ($NaHSO_3$), potassium bisulfite ($KHSO_3$), lithium bisulfite ($LiHSO_3$) and magnesium bisulfite ($Mg(HSO_3)_2$). A preferred metal bisulfite reactant is sodium bisulfite. The amount of metal bisulfite reactant employed typically ranges from about 0.85 equivalents to about 1.2 equivalents, relative to the compound of formula III. The preferred amount of metal bisulfite reactant is typically about 0.90 to 1.1 and is most preferably about 0.95 to 1.0 equivalents. The reaction may be performed for from 2 to about 15 hours at a temperature range from room temperature to about 55° C. It is preferred to conduct the reaction for a time of between about 2 and 5 hours at a temperature of between about 35° C. and about 50° C.

When the reaction is complete, different amounts of various sulfonic acid metal cation salt products are created depending on the makeup of the mixture which contained the compound of formula III. The major component is the sulfonic acid metal cation salt of formula IV. Typically, the major component compound of formula IV will precipitate out of the product mixture spontaneously, but where spontaneous crystallization does not occur, it is possible by careful adjustment of the solvent volumes to cause the major component to crystallize. Usually, the amount of ethyl acetate relative to both the ethanol and water is increased in order to force the precipitation of the major component sulfonic acid metal cation salt. This technique of adjustment of solvent volumes is well known to those skilled in the art. Once precipitated, the desired major component sulfonic acid metal cation salt of formula IV may then be collected via filtration.

The preferred compounds of formula IV are:

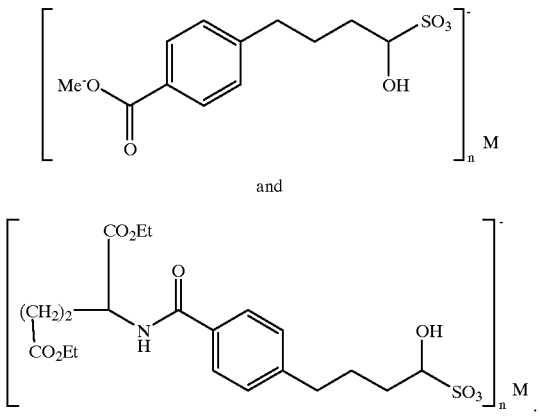

and

Application of the above chemistry enables the synthesis of the compounds of formula IV, which include, but are not limited to:

1-hydroxy-3-(4-carbomethoxyphenyl)propanesulfonic acid sodium salt;

1-hydroxy-3-(4-carboethoxyphenyl)propanesulfonic acid potassium salt;

1-hydroxy-2,3-dimethyl-4-(4-carbomethoxyphenyl) butanesulfonic acid lithium salt;

N-(4-[(3-hydroxy-3-sulfonic acid sodium salt)propyl] benzoyl)-L-glutamic acid dimethyl ester;

N-(4-[(3-hydroxy-3-sulfonic acid potassium salt)propyl] benzoyl)-L-glutamic acid diethyl ester;

N-(4-[(1,2-dimethyl-4-hydroxy-4-sulfonic acid lithium salt)butyl]benzoyl)-L-glutamic acid dipropyl ester;

Compounds of formula III may be prepared from compounds of formula IV by a novel process shown in Scheme 2 below where M, n, $R^2$, and X are as defined above for formula IV.

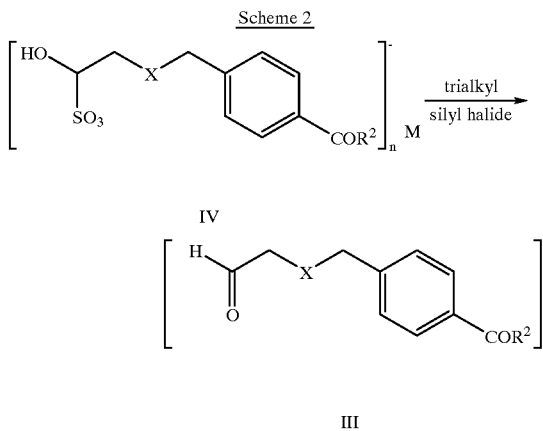

Compounds of formula IV can be converted to aldehydes of formula III by dissolving or suspending a compound of formula IV in a suitable solvent and adding a trialkyisilyl halide. Suitable solvents include, but are not limited to, acetone, tetrahydrofuran, diethylether, methylene chloride, methyl acetate, ethyl acetate, chloroform, mixtures thereof, and the like. The preferred solvent is typically acetonitrile. It has been found that yields for this reaction can be increased by degassing the solution containing the compound of formula IV, before the addition of the trialkylsilyl chloride, with an inert gas. Typically, nitrogen is employed as the inert gas. The preferred trialkylsilyl halide is usually trimethylsilyl chloride. The trialkylsilyl halide is typically employed in a stoichiometric excess. For example, a 2 to 4 stoichiometric excess, relative to the compound of formula IV is typically employed. A 2.7 to about 2.9 stoichiometric excess is usually preferred. The mixture is typically allowed to react for from about fifteen minutes to about one hour. The reaction is usually performed at an elevated temperature of at least about 30° C., preferably at least about 40° C., more preferably at least about 50° C., and most preferably the mixture is allowed to run at between about 60° C. and 70° C.

Although isolation and purification of the compounds of formula III formed by the overall novel process of this invention is possible, these compounds are typically not substantially purified but are instead converted to 5-substituted pyrrolo[2,3-d]pyrimidine compounds of formula VII(a) by the process shown in Scheme 3 below where $R^2$ and X are as defined above for formula IV.

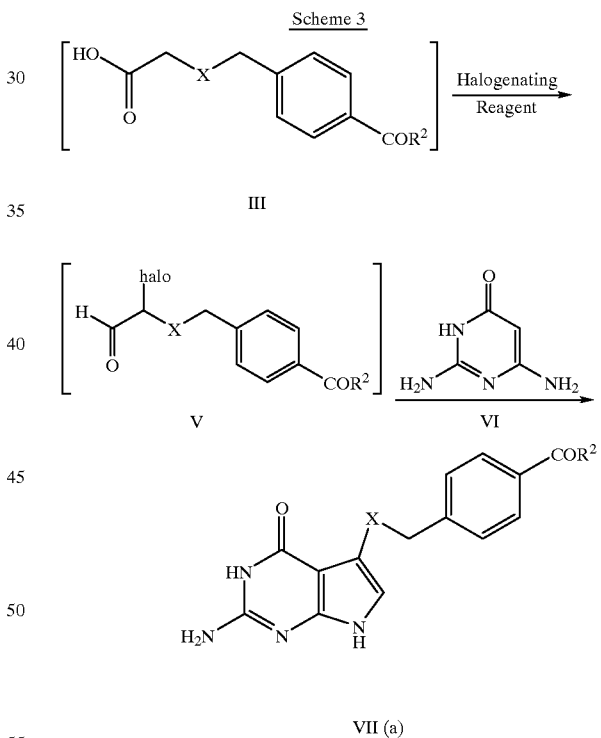

Compounds of formula V may be prepared by adding a halogenating reagent to the solution containing the compound of formula III prepared as described in Scheme 2. The addition may occur at the preferred 60° C. to 70° C. reaction temperature of the previous reaction but the reaction is preferably cooled before the addition of the halogenating reagent. The addition of the halogenating reagent may be done at a temperature of from 0° C. to 60° C., but it has been found that an addition temperature of about 35° C. to about 45° C. is preferred. Once the halogenating agent is added, the resulting mixture is stirred for from about 5 minutes to about 2 hours. In general, time for the halogenation reaction is from about 5 minutes to about 1 hour, but is preferably performed in 20 minutes or less. The preferred halo substituent in compounds of formula V is bromo and the preferred halogenating agent is typically elemental bromine. Once the reaction is complete, it may be quenched by the addition of an aqueous solution of a known halogen scavenger such as sodium bisulfite. The compound of formula V may then be extracted into a suitable, aqueous immiscible organic solvent. This solution which contains the compound of formula V is of high purity and may be used directly to prepare compounds of formula VII(a) or compounds of formula VII:

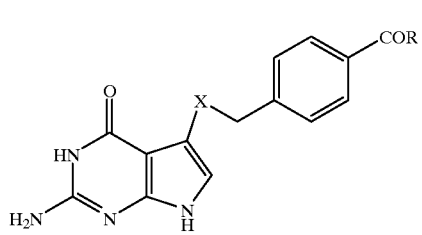

and their pharmaceutical salts and solvates; by following the procedures described in U.S. Pat. No. 5,416,211, the teachings of which are herein incorporated by reference.

When any of the compounds of formula II, IV, IV, VII, or VII(a) contain carboxy protecting groups, they may be removed by well known methods in the art. Numerous reactions for the installation and removal of the carboxy protecting groups contemplated within the scope of this invention are described in a number of standard works including, for example *The Peptides*, Vol. I, Schrooder and Lubke, Academic Press (London and New York, 1965) and the Greene reference cited above. Methods for removing preferred carboxy protecting groups, particularly methyl and ethyl groups, are essentially as described in Examples 5 and 7 infra.

When R is NHCH($CO_2R^1$)$CH_2CH_2CO_2R^1$ in compounds of formula VII or when $R^2$ is NHCH($CO_2R^3$)$CH_2CH_2CO_2R^3$ in compounds of formula II, IV, IV, or VII(a), the R or $R^2$ group can be installed at any convenient point in the synthesis. For example, the glutamic acid residue may be installed after the reactions of Schemes 1–3 essentially as described in Examples 5 and 6 infra. In the alternative, a commercially available glutamic acid dialkyl ester of the formula $NH_2CH(CO_2R^3)CH_2CH_2CO_2R^3$ may be coupled with a commercially available p-halobenzoic acid before subsequent reaction in Scheme 1.

The optimal time for performing the reactions of Schemes 1–3 can be determined by monitoring the progress of the reaction by conventional chromatographic techniques. Choice of reaction solvent is generally not critical so long as the solvent employed is inert to the ongoing reaction and sufficiently solubilizes the reactants to afford a medium within which to effect the desired reaction. Unless otherwise indicated, all of the reactions described herein are preferably conducted under an inert atmosphere. The preferred inert atmosphere is nitrogen.

The process illustrated in Scheme 1 for preparing the novel compounds of formula IV greatly simplifies the purification of compounds of formula III formed by the alkenol coupling to an aryl halide. The process illustrated in Scheme 2 is a previously unknown method of generating aldehydes from sulfonic acid metal cation salts. That conversion is expected to be generally applicable and has great potential for general synthetic utility. Specific to this case, the conversion generates selectively and cleanly the compounds of formula III. In addition, the compounds of formula IV, which can be considered aldehyde analogues in the context of this invention, are stable, usually crystalline materials amenable to bulk manufacture, purification, and storage. Thus, in general, commercial processes which require aldehydes of the formula III, or similar aldehydes, are made simpler by the overall process of the present invention.

The following examples are illustrative only and are not intended to limit the scope of the invention in any way. The terms and abbreviations used in the instant examples have their normal meanings unless otherwise designated. For example "° C.", "N", "mmol", "g", "d", "mL", "M", "HPLC", "$^1$H-NMR", "$^{13}$C—NMR", and "vol." refers to degrees Celsius, normal or normality, millimole or millimoles, gram or grams, density, milliliter or milliliters, molar or molarity, high performance liquid chromatography, proton nuclear magnetic resonance, carbon-13 nuclear magnetic resonance, and an amount in mL/grams relative to starting material respectively. In addition, the absorption maxima listed for the IR spectra are only those of interest and not all of the maxima observed.

EXAMPLES

Example 1

4-(4-Carbomethoxyphenyl)butanal

The Deloxan® THP Type 2 Resin used below was pretreated by mixing it with isopropyl alcohol (2.0 vol. 20 mL) and washing with ethyl acetate (4.0 vol., 40 mL). The organic layer/resin slurry was then filtered before subsequent use as described below.

4-Bromobenzoic acid, methyl ester (60.0 g, 279.00 mmol), lithium acetate dihydrate (31.31 g, 306.90 mmol), lithium chloride (35.48 g, 837 mmol), and tetrabutylammonium chloride (41.22 grams, 131.49 mmol) were added to dimethylformamide (698 mL). The resulting solution was degassed with a subsurface nitrogen purge. 3-buten-1-ol (24.19 grams, 28.81 mL, 334.81 mmol) and palladium acetate (1.57 grams, 6.98 mmol) were added and the reaction mixture was heated to 65° C. with stirring for approximately 10 hours. Reaction completion was indicated by starting material consumption (less than 0.4% 4-bromobenzoic acid, methyl ester remaining) as shown by HPLC (reverse phase, 60% acetonitrile:2.5% acetic acid buffer). The reaction mixture was cooled to 25° C.–30° C. and water (700 ml) and ethyl acetate (700 mL) were added. The reaction mixture was stirred for 10 minutes and subsequently the layers were allowed to separate. The organic layer was separated and retained and the aqueous layer was extracted two additional times with ethyl acetate (720 mL). The ethyl acetate washes were combined with the original organic layer and the combined organic layers were washed with brine (350 mL). The organic layer was filtered, to remove elemental palladium, and slurried with Deloxan® THP Type II Resin (3.0 grams dry weight) for 45 minutes. The title compound was obtained as a solution in ethyl acetate, in approximately 87% yield. A small amount of ethyl acetate solution was concentrated for characterization of product.

Analytical Data:

$^1$H NMR:($d_6$-DMSO) δ 9.65 (t, J=1.5 Hz, 1H), 7.86 (d, J=8.5 Hz, 2H), 7.32 (d, J=8.5 Hz, 2H), 3.82 (s, 3H), 2.63 (t, J=7.7 Hz, 2H), 2.43 (td, J=7.4, 1.5 Hz, 2H), 1.82 (m, 2H).

$^{13}$C—NMR: ($d_6$-DMSO) δ 203.1, 166.2, 147.4, 129.3, 128.7, 127.4, 51.9, 42.4, 34.3, 23.0.

Example 2

1-Hydroxy-4-(4-Carbomethoxyphenyl) butanesulfonic Acid Sodium

Salt

The ethyl acetate extracts from Example 1 were concentrated to 3.6 vol. (8.7 mL) in vacuo at about 37° C. 3A Alcohol (3 vol., 7.2 mL) and water (0.63 vol., 1.51 mL) were added followed by sodium bisulfite (1.04 g, 10.03 mmol). The reaction mixture was stirred for approximately 8 hours. After 10 minutes crystallization of the sulfonic acid began. Reaction completion was determined by $^1$H NMR analysis of the reaction mixture filtrate. The resulting white slurry is filtered to afford the title compound (2.78 grams, 8.98 mmol) as a white crystalline solid in approximately 80% yield. The filter cake was washed with ethanol (1.8 vol.) and dried in vacuo at 40° C. Isomeric impurities were non-detectable by NMR.

Analytical Data:

$^1$H—NMR: ($d_6$-DMSO) δ 7.86 (d, J=8.27 Hz, 2H), 7.32 (d, J=8.27 Hz, 2H), 5.33 (d, J=2.3 Hz, 1H), 3.84 (m, 1H), 3.81 (s, 3H), 2.63 (m, 2H), 1.75 (m, 1H), 1.73 (m, 1H), 1.61 (m, 1H), 1.48 (m, 1H).

$^{13}$C—NMR: ($d_6$-DMSO) δ 166.2, 148.3, 129.2, 128.7, 127.1, 82.7, 51.9, 35.1, 31.2, 27.2.

IR: (run as KBr pellet) 3237, 2962, 2930, 2889, 1726 cm$^{-1}$.

Example 3

1-Hydroxy-2-Bromo-4-(4-Carbomethoxyphenyl) butanal

To a 50 mL round bottom flask with magnetic stirrer were added 4-(4-oxobutyl)-benzoic acid methyl ester sodium bisulfite adduct (3.10 grams, 10 mmol), acetonitrile (14 mL) and chlorotrimethylsilane (3.6 mL, 28 mmol). Nitrogen gas was bubbled through for five minutes and then the mixture was heated in a 60° C. bath for one hour under nitrogen. The mixture at this point in time was a light yellow. The mixture was then cooled under refrigeration to 5° C. and bromine (0.5 mL, 9.7 mmol,) was added. The brownish bromine color was discharged within 1 minute. The solution was light yellow and the visible solids appeared colorless. The mixture was removed from the cooling bath and stirred for an additional 2 hours. Water (14 mL) and sodium bisulfite (0.14 grams) were added to scavenge/quench the remaining bromine and the resulting mixture stirred for 1 hour. The mixture was then partitioned between methylene chloride (14 mL) and an additional 7 mL of water. The organic phase was separated and stripped on a rotary evaporator until only 26 mL remained. Within this 26 mL is the title compound which was not purified or isolated further before subsequent reaction as in Example 4 below. A small amount of the methylene chloride solution was concentrated for characterization of product.

Analytical Data:

$^1$H—NMR: (CDCl$_3$) δ 9.40 (d, 1H), 7.95 (d, 2H), 7.26 (d, 2H), 4.15 (ddd, 1H), 3.88 (s, 3H), 2.89 (m, 1H), 2.79 (m, 1H), 2.35 (m, 1H), 2.21 (m, 1H).

$^{13}$C—NMR: (CDCl$_3$) δ 191.4, 166.8, 145.1, 129.9, 128.5, 128.5, 54.4, 52.0, 32.7, 32.6.

Example 4

4-[2-(2-Amino-4,7-Dihydro-4-Oxo-1H-Pyrrolo[2,3-d]pyrimidin-5-yl)ethyl]benzoic Acid Methyl Ester The 26 mL of organic layer from Example 3, which contains 1-hydroxy-2-bromo-3-(4-carbomethoxyphenyl) butanal, had added to it 2,4-diamino-6-hydroxy pyrimidine (1.26 grams, 10 mmol), sodium acetate (1.68 grams, 20 mmol) and water (23 mL). Nitrogen was bubbled through this reaction mixture for 5 minutes. The mixture was heated at 40° C. under N$_2$ for 2 hours. The mixture was cooled to ambient conditions and filtered and the collected solids were washed with 23 mL of a 1:1 mixture of acetonitrile and water. The filter cake was dried to yield 1.47 grams of light yellow needles. The analysis showed a 45% overall yield for Examples 3 and 4 and also showed the title compound was produced at a purity level of 94.8% by HPLC (reverse phase, gradient 50% to 30% methanol:20 mM potassium dihydrogen phosphate or ammonium dihydrogen phosphate buffer).

Analytical Data:

$^1$H—NMR ($d_6$-DMSO) δ 10.66 (s, 1H), 10.23 (s, 1H), 7.84 (d, 2H), 7.32 (d, 2H), 6.31 (s, 1H), 6.08 (s, 2H), 3.80 (s, 3H), 2.98 (dd, 2H), 2.86 (dd, 2H).

$^{13}$C—NMR ($d_6$-DMSO) δ 166.3, 159.4, 152.3, 151.3, 148.4, 129.2, 128.7, 127.1, 117.6, 113.6, 98.8, 52.0, 36.3, 27.9.

Example 5

4-[2-(2-Amino-4,7-Dihydro-4-Oxo-1H-Pyrrolo[2,3-d]pyrimidin-5-yl)ethyl]benzoic Acid A flask was charged with 13.0 grams of 4-[2-(2-amino-4,7-dihydro-4-oxo-1H-pyrrolo[2,3-d]pyrimidin-5-yl)ethyl] benzoic acid, methyl ester and 150 mL of 2N aqueous sodium hydroxide solution. Stirring was applied and the slurry was heated to 40° C. The reaction was monitored by HPLC (reverse phase, gradient 50% to 30% methanol:20 mM potassium dihydrogen phosphate or ammonium dihydrogen phosphate buffer). 3A Alcohol (230 mL) was added to the solution, which was then seeded with authentic 4-[2-(2-amino-4,7-dihydro-4-oxo-1H-pyrrolo[2,3-d] pyrimidin-5-yl)ethyl]benzoic acid (obtained by following the procedure of U.S. Pat. No. 5,416,211). The solution pH was adjusted to 4.4 with 6N hydrochloric acid (48.5 mL). The solids were filtered off and washed with 30 mL of a 1:1 mixture of water:3A alcohol. The solids were dried in vacuo at 50° C. 10.84 grams of the title compound were recovered.

Analytical Data:

$^1$H NMR ($d_6$-DMSO) δ 10.66 (br s, 1H), 10.33 (br s, 1H), 7.83 (d, 2H), 7.30 (d, 2H), 6.31 (s, 1H), 6.17 (br s, 2H), 2.97 (m, 2H), 2.85 (m, 2H).

$^{13}$C—NMR ($d_6$-DMSO) δ 167.6, 159.5, 152.4, 151.4, 147.9, 129.4, 128.6, 128.4, 117.7, 113.6, 98.8, 36.4, 28.0.

Example 6

N-(4-[2-(2-Amino-4,7-Dihydro-4-Oxo-1H-Pyrrolo[2,3-d]pyrimidin-5-yl)ethyl]benzoyl)-L-Glutamic Acid Diethyl

Ester p-Toluenesulfonic Acid Salt

A 50 mL flask with mechanical stirrer, thermometer and N$_2$ adapter was charged with 1.93 g (corrected for assay) of 4-[2-(2-amino-4,7-dihydro-4-oxo-1H-pyrrolo[2,3-d] pyrimidin-5-yl)ethyl]benzoic acid (2.5 g, potency 77%) and 13.5 mL of dimethylformamide. The slurry was stirred 15 minutes and 1.94 grams of N-methylmorpholine (2.9 eq) was added. The mixture was cooled to 5° C. with an ice/water bath and chlorodimethoxytriazine (1.46 grams, 1.28 eq.) was added all at once. The mixture was stirred 40 minutes before L-glutamic acid diethyl ester (1.99 g, 1.28 eq) was added all at once. The reaction was allowed to warm to ambient temperature. The reaction was monitored by HPLC (reverse phase, gradient 20% to 46% acetonitrile:0.5% acetic acid buffer) and was complete in 1 hour at 23° C. The reaction mixture was transferred to a 250 mL Erlenmeyer flask containing 36 mL of deionized water and 18 mL of methylene chloride. The reaction flask was rinsed with 18 mL of methylene chloride which was added to the Erlenmeyer flask. The mixture was stirred 15 minutes and the layers were allowed to separate. The methylene chloride layer was concentrated from 46 grams to 13 grams using a rotary evaporator at reduced pressure at a bath temperature at 45° C. The concentrate was diluted with 55 mL of 3A alcohol, and concentrated again to 10 grams to remove methylene chloride. The concentrate was diluted to a total volume of 60 mL with 3A alcohol and the resulting solution was heated to 70° C. to 75° C. p-Toluenesulfonic acid (3.16 g, 2.57 eq.) dissolved in 55 mL of 3A alcohol were added over 30–90 minutes. The resulting slurry was refluxed for an hour.

The slurry was cooled to ambient temperature and filtered using a 7 cm Buchner funnel. The wet cake was washed with 25 mL ethanol and dried in vacuo at 50° C. overnight to yield 3.66 grams of the title compound. Potency 95%

Analytical data:

$^1$H NMR (d$_6$ DMSO) δ 11.59 (br s, 1H), 11.40(s, 1H), 8.66 (d, 1H), 7.88(br s, 1H), 7.79 (d, 2H), 7.58 (d, 2H), 7.29 (d, 2H), 7.16 (d, 2H), 6.52 (s, 1H), 4.42 (m, 1H), 4.09 (q, 2H), 4.03 (q, 2H), 2.94 (m, 2H), 2.89 (m, 2H), 2.43 (m, 2H), 2.28 (s, 3H), 2.08 (m, 1H), 2.02 (m, 1H), 1.17 (t, 3H), 1.14 (t, 3H).

$^{13}$C NMR (d$_6$ DMSO) δ 172.3, 171.9, 166.7, 157.2, 150.6, 145.8, 144.4, 138.6, 138.3, 131.3, 128.4, 128.3, 127.5, 125.6, 119.2, 115.4, 99.1, 60.6, 60.0, 52.0, 35.8, 30.2, 27.2, 25.8, 20.8, 14.1, 14.1.

Example 7

N-[4-[2-(2-Amino-4,7-Dihydro-4-Oxo-1H-Pyrrolo[2,3-d]pyrimidin-5-yl)ethyl]benzoyl]-L-Glutamic Acid To 1.00 gram of N-[4-[2-(2-amino-4,7-dihydro-4-oxo-1H-pyrrolo[2,3-d]pyrimidin-5-yl)ethyl]benzoyl]-L-glutamic acid, diethyl ester p-toluenesulfonic acid salt in a 50 ml Erlenmeyer flask was added 1N aqueous sodium hydroxide (6.7 mL) and the resulting mixture stirred until all the solids had dissolved (approximately 20 minutes). The solution was light green. An additional 6–7 mL of deionized water was added and the pH was adjusted to 2.8–3.1 with dilute hydrochloric acid. The resulting slurry was heated to approximately 70° C. in order to produce larger particles of solids. The solids were filtered to yield the title compound.

Example 8

N-(4-[2-(2-Amino-4,7-Dihydro-4-Oxo-1H-Pyrrolo[2,3-d]pyrimidin-5yl)ethyl]benzoyl)-L-Glutamic Acid Disodium Salt N-[4-[2-(2-Amino-4,7-dihydro-4-oxo-1H-pyrrolo[2,3-d]pyrimidin-5-yl)ethyl]benzoyl]-L-glutamic acid from Example 7 was dissolved in 3.8 mL of water and 2.2 ml of 1N sodium hydroxide. The pH of the mixture was adjusted to 7.5–8.5 using dilute hydrochloric acid and 1N sodium hydroxide. The solution was heated to 70° C. and 40 mL of 3A alcohol were added. The solution was allowed to cool to room temperature during which time a thick slurry developed. The solids were filtered and washed with 4:1 ethanol:water. The solids were dried at 50° C. in a vacuum oven. 640 milligrams of the title compound were recovered as a solid.

Analytical Data:

$^1$H NMR (300 MHz, DMSO-d$_6$/D$_2$O) δ 7.67 (d, J=7.8 Hz, 2H), 7.22 (d, J=7.8 Hz, 2H), 6.30 (s, 1H), 4.09 (m, 1H), 2.88 (m, 2H), 2.83 (m, 2H), 2.05–1.71 (m, 4H).

$^{13}$C NMR (75 MHz, DMSO-d$_6$/D$_2$O) δ 179.9, 176.9, 167.1, 160.8 152.9, 151.7, 146.7, 132.6, 129.4, 127.9, 118.7, 115.2, 99.5, 56.1, 36.8, 35.3, 30.1, 28.4.

Example 9

1-Hydroxy-4-(L-N-[1,3-Dicarboethoxypropyl]benz-4-amide)butanesulfonic Acid Sodium Salt L-N-1,3-(Dicarboethoxypropyl)-4-iodobenzamide (10.00 g, 23.1 mmol), lithium chloride (2.937 g, 69.3 mmol), lithium acetate (2.592 g, 25.4 mmol), tetrabutylammonium chloride (3.412 g, 11.55 mmol) and dimethylformamide (57.7 mL) were combined. The mixture was thoroughly sparged with nitrogen. 3-buten-1-ol (1.998 g, 27.7 mmol) and palladium(II)acetate (0.130 g, 0.577 mmol) were added. The mixture was heated to 60° C. under nitrogen for 24 hours. At this point HPLC (reverse phase, 60% acetonitrile:2.5% acetic acid buffer) indicated reaction completion. The reaction was partioned between ethyl acetate (58 mL) and water (58 mL). The layers were separated. The aqueous layer was extracted twice with ethyl acetate (58 mL per extraction). The organic layers were combined and washed with brine (30 mL). The resulting organic layer was concentrated to 25 mL. Ethyl acetate (15 mL), water (3.25 mL), and sodium bisulfite (0.636 g, 6.11 mmol) were added. The mixture was stirred at 25° C. for 16 hours. Acetone (75 mL) was added. The product precipitate was collected by filtration and dried in a vacuum oven to give 1.59 g of the title compound. Yield: 48.6%.

Example 10

N-(4-[2-(2-Amino-4,7-Dihydro-4-Oxo-1H-Pyrrolo[2,3-d]pyrimidin-5-yl)ethyl]benzoyl)-L-Glutamic Acid Diethyl Ester In a 25 mL round bottom flask with magnetic stirring were combined 1-hydroxy-4-(L-N-[1,3-dicarboethoxypropyl]benz-4-amide)butanesulfonic acid sodium salt (0.922 g, 2.0 mmol), acetonitrile (5 mL) and trimethylsilyl chloride (0.72 mL). The mixture was sparged with nitrogen for 5 minutes, and then heated to 60° C. for 1 hour. The temperature was adjusted to 40° C. and bromine (98 μL, 1.9 mmol) was added. $^1$H—NMR indicated clean conversion to the α-bromide intermediate. The reaction was cooled to ambient and washed with 1% aqueous sodium bisulfite solution (2.5 mL). The organic phase was stripped to an oil. 2,4-diamino-6-hydroxypyrimidine (300 mg, 2.4 mmol), sodium acetate (500 mg), water (5 mL), and acetonitrile (5 mL) were added. The mixture was heated at 40° C. for 6 hours. The upper, organic phase was collected and concentrated to an oil (450 mg). $^1$H—NMR and HPLC (reverse phase, gradient 20% to 46% acetonitrile:0.5% acetic acid buffer) confirmed that the oil was predominately the title compound.

The present invention has been described in detail, including the preferred embodiments thereof. However, it will be appreciated that those skilled in the art, upon consideration of the present disclosure, may make modifications and/or improvements that fall within the scope and spirit of the invention as set forth in the following claims.

We claim:

1. A compound of formula IV:

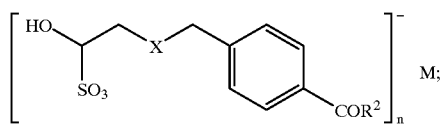

wherein:
M is a metal cation;
n is 1 or 2;
$R^2$ is $NHCH(CO_2R^3)CH_2CH_2CO_2R^3$ or $OR^3$;
$R^3$ is independently at each occurrence a carboxy protecting group; and
X is a bond or $C_1$–$C_4$ alk-diyl.

2. The compound according to claim 1 wherein X is a bond, —$CH_2$—, or —$CH_2CH_2$— and $R^2$ is $NHC^*H(CO_2R^3)CH_2CH_2CO_2R^3$ or $OR^3$ where the configuration about the carbon atom designated * is L.

3. The compound according to claim 2 wherein X is —$CH_2$—.

4. The compound according to claim 1 wherein M is an alkali metal cation and n is 1 and $R^2$ is $NHC^*H(CO_2R^3)CH_2CH_2CO_2R^3$ or $OR^3$ where the configuration about the carbon atom designated * is L.

5. The compound according to claim 4 wherein the alkali metal is sodium.

6. The compound according to claim 1 wherein M is sodium, n is 1, X is —$CH_2$—, and $R^2$ is $NHC^*H(CO_2R^3)CH_2CH_2CO_2R^3$ or $OR^3$ where the configuration about the carbon atom designated * is L.

7. A process for preparing a compound of formula IV:

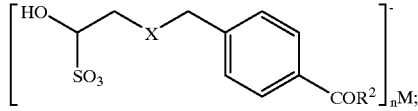

wherein:
M is a metal cation;
n is 1 or 2;
$R^2$ is $NHCH(CO_2R^3)CH_2CH_2CO_2R^3$ or $OR^3$;
$R^3$ is independently at each occurrence a carboxy protecting group;
X is a bond or $C_1$–$C_4$ alk-diyl;
comprising:
reacting a compound of formula III:

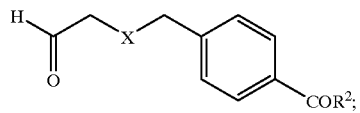

wherein:
$R^2$ and X are as defined above for formula IV;
with a compound of the formula $M(HSO_3^-)_n$:
wherein:

M is defined above for formula IV; and
n is 1 or 2;
in a solvent.

8. The process according to claim 7 wherein the compound of formula III is a compound wherein X is a bond, —$CH_2$—, or —$CH_2CH_2$— and $R^2$ is $NHC^*H(CO_2R^3)CH_2CH_2CO_2R^3$ or $OR^3$ where the configuration about the carbon atom designated * is L.

9. The process according to claim 8 wherein X is —$CH_2$—.

10. The process according to claim 9 wherein the compound of the formula $M(HSO_3^-)_n$ is a compound wherein M is an alkali metal cation and n is 1 and the reaction is performed at a temperature between 35° C. and 50° C.

11. The process according to claim 10 wherein the alkali metal is sodium.

12. The process according to claim 7 wherein the solvent is a mixture of ethyl acetate, 3A-ethanol, and water.

13. The process according to claim 7 further comprising:
reacting a compound of formula I:

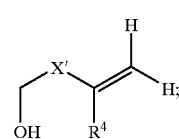

wherein:
$R^4$ is hydrogen or $C_1$–$C_4$ alkyl; and
X' is a bond or $C_1$–$C_4$ aik-diyl;
with the proviso that if X' is not a bond, then the carbon alpha to the alcohol must be a —$CH_2$— moiety;
with a compound of formula II:

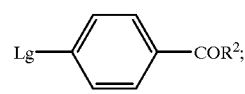

wherein:
$R^2$ is defined above for formula IV; and
Lg is a leaving group;
in a solvent, in the presence of a palladium catalyst and a phase transfer catalyst, and optionally in the presence of a metal cation chloride, to afford a compound of formula III.

14. The compound according to claim 1 which is:

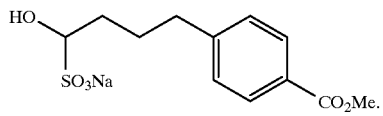

15. The compound according to claim 1 which is 1-hydroxy-4-(4-carbomethoxyphenyl) butanesulfonic acid sodium salt.

* * * * *